United States Patent
Ladnak et al.

(10) Patent No.: US 11,028,042 B2
(45) Date of Patent: Jun. 8, 2021

(54) PROCESS FOR PREPARING AN AROMATIC POLYAMINE MIXTURE

(71) Applicant: BASF SE, Ludwigshafen am Rhein (DE)

(72) Inventors: Viktor Ladnak, Ludwigshafen (DE); Silvia Tauro, Ludwigshafen (DE); Kerstin Heinen, Ludwigshafen (DE); Kai Thiele, Antwerp (BE); Klaus-Peter Metzner; Torsten Mattke, Ludwigshafen (DE)

(73) Assignee: BASF SE

( * ) Notice: Subject to any disclaimer, the term of this patent is extended or adjusted under 35 U.S.C. 154(b) by 392 days.

(21) Appl. No.: 16/071,309

(22) PCT Filed: Jan. 12, 2017

(86) PCT No.: PCT/EP2017/050517
§ 371 (c)(1),
(2) Date: Jul. 19, 2018

(87) PCT Pub. No.: WO2017/125302
PCT Pub. Date: Jul. 27, 2017

(65) Prior Publication Data
US 2020/0339501 A1    Oct. 29, 2020

(30) Foreign Application Priority Data
Jan. 20, 2016 (EP) .................................... 16152074

(51) Int. Cl.
*C07C 209/78* (2006.01)
*C07C 209/88* (2006.01)
*B01D 3/14* (2006.01)

(52) U.S. Cl.
CPC ............ *C07C 209/78* (2013.01); *B01D 3/141* (2013.01); *B01D 3/143* (2013.01); *C07C 209/88* (2013.01); *C07B 2200/07* (2013.01)

(58) Field of Classification Search
CPC ...... C07C 209/78; C07C 209/88; B01D 3/141
See application file for complete search history.

(56) References Cited

U.S. PATENT DOCUMENTS

| | | | |
|---|---|---|---|
| 3,860,637 A | 1/1975 | Bentley | |
| 6,433,219 B1 | 8/2002 | Ströfer et al. | |
| 7,230,130 B2 | 6/2007 | Ströfer et al. | |
| 7,312,362 B2 * | 12/2007 | Keggenhoff | .......... C07C 209/78 564/397 |
| 8,703,997 B2 * | 4/2014 | Schneider | ............. C07C 209/36 560/347 |
| 2002/0132953 A1 | 9/2002 | Ströfer et al. | |
| 2005/0014975 A1 | 1/2005 | Ströfer et al. | |
| 2009/0240077 A1 | 9/2009 | Wershofen et al. | |

FOREIGN PATENT DOCUMENTS

| | | |
|---|---|---|
| DE | 198 04 915 A1 | 8/1999 |
| EP | 1 167 343 A1 | 1/2002 |

OTHER PUBLICATIONS

International Search Report dated Apr. 4, 2017 in PCT/EP2017/050517.

* cited by examiner

*Primary Examiner* — Sikarl A Witherspoon
(74) *Attorney, Agent, or Firm* — Faegre Drinker Biddle & Reath LLP

(57) ABSTRACT

A process for preparing an aromatic polyamine mixture including 4,4'-methylenedi(phenylamine) and higher homologues of MDA is provided. The process includes steps of (i) reaction of aniline with formaldehyde by means of an acid catalyst to form a crude product mixture (I), (ii) neutralization of the crude product mixture (I) and removal of the salts formed; (iii) isolation of aniline; (iv) distillation of the resulting crude product mixture so as to separate off (iv-1) a mixture (II) of MDA isomers (II-1) containing from 8 to 20% by weight of 4,4'-methylenedi(phenylamine) and not more than 0.3% by weight of secondary components (II-2) and (iv-2) a low boiler mixture of at least 55% by weight of secondary components (II-2) and MDA isomers (II-1); and (v) recirculation of the mixture (II).

10 Claims, 1 Drawing Sheet

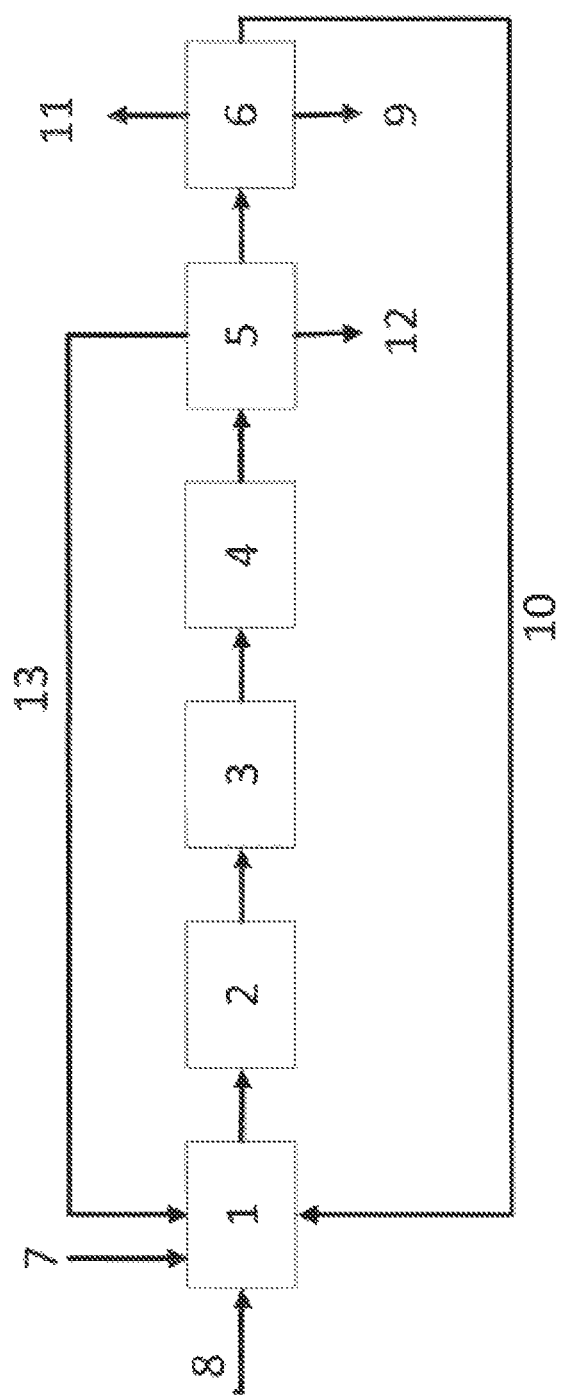

PROCESS FOR PREPARING AN AROMATIC POLYAMINE MIXTURE

The invention relates to a process for preparing an aromatic polyamine mixture comprising essentially 4,4'-methylenedi(phenylamine) and higher homologues of methylenedi(phenylamine).

The preparation of methylenedi(phenylamine) (=MDA) is usually carried out by continuous or batchwise reaction of aniline with formaldehyde in the presence of acid catalysts. This reaction gives a mixture composed of predominantly 4,4'-MDA, 2,4'-MDA, 2,2'-MDA and higher homologues of MDA, which mixture is referred to as "crude MDA". However, the isomers 2,4'-MDA and 2,2'-MDA are often undesirable since in a subsequent reaction with phosgene the compounds 2,4'- and 2,2'-methylenedi(phenyl isocyanate) (=MDI) are formed. These compounds have isocyanate groups in the ortho position and these react only incompletely in a urethane formation reaction with polyols.

Various methods of reducing the content of 2,4'-MDA and 2,2'-MDA in crude MDA are known.

US-A 2009/0240077 discloses a process for preparing diamines and polyamines of the diphenylmethane series by reaction of aniline and formaldehyde in the presence of an acid catalyst, where the aniline used comprises less than 0.5% by weight of compounds comprising carbonyl groups. Excess aniline is removed from the organic phase of the resulting reaction product by distillation and at least partly recirculated to the reaction. The diamines and polyamines obtained have improved color values. However, a disadvantage is that the process has a low selectivity and the content of 4,4'-MDA and its higher homologues is thus in need of improvement.

U.S. Pat. No. 3,860,637 describes a process for preparing polyamines, in particular 4,4'-MDA, by reaction of aniline with formaldehyde to give a crude product mixture, with a stream of 2,2'-MDA and 2,4'-MDA being separated off and recirculated into the aniline-formaldehyde stream. The 2,2' and 2,4' isomers are separated off by means of a vacuum distillation under conditions which are not specified further.

EP-A-1167343 describes a process for preparing an aromatic polyamine mixture comprising 4,4'-methylenedi(phenylamine) and higher homologues of methylenedi(phenylamine), in which aniline is reacted with formaldehyde in the presence of a catalyst in stage I in a plant comprising a mixing zone (a), a condensation zone (b) and a rearrangement zone (c) to give a crude product mixture. Aniline and water are separated off from the crude product mixture and a mixture of 2,2'-methylenedi(phenylamine) and 2,4'-methylenedi(phenylamine) is then separated off from the resulting aniline-depleted crude product mixture by distillation. The mixture of 2,2'-MDA and 2,4'-MDA is separated off by means of a distillation column which has at least 40 theoretical plates at a temperature of from 180 to 280° C., a pressure at the top of from 0.1 to 10 mbar and a pressure at the bottom of from 8 to 20 mbar.

The formaldehyde used is divided into at least two parts of which one part is fed to the condensation zone (b) and one part is mixed with the mixture of 2,2'-methylenedi(phenylamine) and 2,4'-methylenedi(phenylamine) which has been separated off and fed to the rearrangement zone c) of stage I.

A disadvantage of the two abovementioned processes is that the separation of 4,4-MDA and 2,4-MDA by distillation is difficult and leads to high energy costs and capital costs.

A further disadvantage is that the crude MDA obtained comprises low-boiling impurities which, after the distillation of the crude MDA, are recirculated together with the mixture of 2,2-MDA and 2,4-MDA to the reaction with formaldehyde. These secondary components can accumulate in the recycle stream (when they do not react with formaldehyde) or (when they react with formaldehyde) lead to fresh impurities and also to increased concentrations of impurities in the MDI, e.g. an increased concentration of N-methyl-4,4'-methylene dianiline (N-methyl-MDA). These low-boiling impurities often result in the downstream products of polymeric MDI obtained from the target product after the reaction with phosgene having high chlorine values and a dark or yellowish discoloration.

It is therefore an object of the present invention to provide an improved process, in particular a process having reduced energy costs, for preparing an aromatic polyamine mixture by reaction of aniline with formaldehyde, which polyamine mixture comprises essentially 4,4'-methylenedi(phenylamine) and higher homologues of methylenedi(phenylamine), with the process having a very high selectivity to 4,4'-MDA based on 2-ring MDA. In addition, the use of raw materials such as hydrochloric acid or sodium hydroxide should be significantly reduced by the process. A further object is that the product obtained by the process should be largely free of secondary components, in particular N-methyl-MDA, and the downstream products of polymeric MDA obtained from the target product should have improved color values and also chlorine values.

For the purposes of the invention, 2-ring MDA encompasses 2,2'-MDA, 2,4'-MDA and 4,4'-MDA. The selectivity to 4,4'-MDA based on 2-ring MDA is defined as follows:

Selectivity (4,4'-MDA)=n (4,4'-MDA)/[n (2,2'-MDA)+n (2,4'-MDA)+n (4,4'-MDA)], where n is the respective molar amount.

The object has been able to be achieved by the inventive process as set forth in the claims.

The invention accordingly provides a process for preparing an aromatic polyamine mixture comprising 4,4'-methylenedi(phenylamine) and higher homologues of methylenedi(phenylamine) by (i) reaction of aniline with formaldehyde by means of an acid catalyst to form a crude product mixture (I), where (i) is carried out in a plant which comprises a mixing zone (a), a condensation zone (b), a rearrangement zone (c) and optionally an after-reaction zone (d);

(ii) neutralization of the crude product mixture (I) obtained in (i) and removal of the salts formed;

(iii) separation of aniline from the crude product mixture obtained in (ii) and optionally recirculation of the aniline to the mixing zone (a); then (iv) distillation of the crude product mixture obtained in (iii) so as to separate off
   (iv-1) a mixture (II) consisting of methylenedi(phenylamine) isomers (II-1) and secondary components (II-2) which are different therefrom, where, based on (II-1), the proportion of 4,4'-methylenedi(phenylamine) is from 8 to 20% by weight and, based on (II), the proportion of secondary components (II-2) is not more than 0.3% by weight, and
   (iv-2) a low boiler mixture which consists of secondary components (II-2) and methylenedi(phenylamine) isomers (II-1) and in which the proportion of the secondary components (II-2) is at least 55% by weight; and (v) recirculation of the mixture (II) to one of the zones (a) to (d), preferably (a).

The polyamine mixture obtained by the process of the invention comprises essentially 4,4'-methylenedi(phenylamine) and higher homologues of methylenedi(phenylamine).

For the purposes of the present invention, this means that the polyamine mixture generally has a content of 4,4'-MDA and higher homologues of MDA of greater than 85% by weight, preferably greater than 90% by weight, particularly preferably greater than 94% by weight, very particularly preferably greater than 95% by weight. The content of 2,2'-MDA and 2,4'-MDA is generally less than 10% by weight, preferably less than 6% by weight and particularly preferably less than 5% by weight.

Higher homologues are, for the purposes of the invention, homologues of methylenedi(phenylamine) having from 3 to 10 rings, in particular from 3 to 4 rings. For the purposes of the invention, the higher homologues are, unless explicitly indicated, also referred to collectively as polymeric MDA (pMDA).

The mixture (II) which is, according to the invention, separated off in step (iv-1) and recirculated in step (v) consists of methylenedi(phenylamine) isomers (II-1) and secondary components (II-2) different therefrom. The proportion of secondary components (II-2) is not more than 0.3% by weight, based on the mixture (II).

The proportion of secondary components (II-2) in the mixture (II) (=recycle stream) is preferably not more than 0.1% by weight, particularly preferably not more than 0.01% by weight. The sum of the components (II-1) and (II-2) in the mixture (II) is 100% by weight.

The methylenedi(phenylamine) isomers (II-1) are, in particular, a mixture of 2,2'-, 2,4'- and 4,4'-methylenedi(phenylamine), where the proportion of 4,4'-methylenedi(phenylamine) is from 8 to 20% by weight, preferably from 9 to 16% by weight, particularly preferably from 10 to 14% by weight. The proportions of the various methylenedi(phenylamine) isomers in the methylenedi(phenylamine) isomer mixture (II-1) add up to 100% by weight.

The secondary components (II-2) do not comprise any methylenedi(phenylamine) isomers (II-1). The secondary components (II-2) are generally compounds which at atmospheric pressure have a boiling point ($T_B$) which is equal to or greater than the boiling point of aniline and less than the boiling point of 2,2-MDA. They are often, without this constituting a restriction, aniline, aminobenzylaniline, methylquinoline, formanilide, methylenecarboxanilide, diphenylamine, 2-aminobiphenyl, N(para-tolyl)phenylamine, 1,2,3,4-tetrahydroacridine, acridinic acid, 9,10-dihydroacridine, N-methyl-4,4'-methylenedianiline and also isomers thereof, in particular aniline, diphenylamine, acridinic acid and dihydroacridines.

The low boiler mixture separated off according to the invention in step (iv-2) consists of at least 55% by weight, preferably at least 80% by weight, particularly preferably at least 90% by weight, of secondary components (II-2) and methylenedi(phenylamine) isomers (II-1), each as defined above, where the sum of the components (II-2) and (II-1) in the low boiler mixture is 100% by weight.

According to the present invention, the reaction (i) of aniline with formaldehyde to form a crude product mixture (I) is carried out in a plant having the reaction zones (a) to (c) and optionally (d), as described below:

(i-a) mixing of aniline or optionally a mixture of aniline and catalyst with formaldehyde in a suitable mixing apparatus. This reaction zone is referred to as mixing zone (a).

(i-b) Reaction in a reaction apparatus, usually in a temperature range from 20 to 100° C., preferably from 30 to 60° C. Here, a condensation of the starting materials to form aminobenzylamines (ABAs), which appear as intermediate product, predominantly takes place. This reaction zone is referred to as condensation zone (b) for the purposes of the present invention.

(i-c) Reaction in a reaction apparatus, usually in a temperature range from 60 to 140° C., preferably from 70 to 100° C. Here, a rearrangement of the aminobenzylamines formed as intermediate to give crude MDA predominantly takes place. This zone is referred to as rearrangement zone (c) for the purposes of the present invention.

(i-d) Reaction in a reaction apparatus, usually in a temperature range from 70 to 180° C., preferably from 80 to 120° C. Here, completion of the abovementioned rearrangement reaction to give crude MDA predominantly takes place. This reaction zone is referred to as after-reaction zone (d) for the purposes of the present invention. Stage (i-d) is optional.

Suitable mixing apparatuses for the reaction zone (a) are, for example, mixing pumps, nozzles and both static and dynamic mixers.

Suitable reaction apparatuses for the reaction zones (b) to (d) are, for example, tube reactors, stirred reactors and reaction columns. Furthermore, the reaction zones (b) to (d) of stage (i) can be present in a single reactor which optionally has different temperature regions. This is possible in, for example, a tray column.

The crude product mixture from the reaction zone (c) or optionally (d) is usually transferred into a work-up zone (e). There, the (ii) neutralization of the crude product mixture (I) obtained in (i) and the removal of the salts formed takes place. The neutralization of the crude product mixture (I) is effected by means of alkali, preferably aqueous NaOH. The salts formed can be separated off in the aqueous phase.

Subsequently, (iii) aniline is separated off from the crude product mixture obtained in (ii) and optionally recirculated to the mixing zone (a). The aniline is separated off by means of conventional methods, in particular by distillation (e.g. rotary evaporator, distillation column, etc.), with the conditions being selected so that aniline is obtained in a purity of at least 95%. The aniline is preferably separated off by means of one or more distillation columns, preferably connected in series. For the aniline distillation, a pressure of from 1 to 9 mbar, preferably from 3 to 8 mbar, particularly preferably from 4 to 6 mbar, at a temperature of from 27 to 110° C., preferably from 43 to 100° C., particularly preferably from 47 to 89° C., measured in the last column at the top of which the aniline is obtained, has been found to be advantageous. Under the abovementioned conditions, aniline can be obtained in a purity of at least 95%, preferably >97%, very particularly preferably >98%.

The aniline which has been separated off is preferably recycled and returned to the mixing zone (a).

This is followed by (iv) the distillation of the resulting low-aniline crude product mixture so as to separate off (iv-1) a mixture (II) consisting of methylenedi(phenylamine) isomers (II-1) and secondary components (II-2) different therefrom, where, based on (II-1), the proportion of 4,4'-methylenedi(phenylamine) is from 8 to 20% by weight and, based on (II), the proportion of secondary components (II-2) is not more than 0.3% by weight, and (iv-2) a low boiler mixture which consists of secondary components (II-2) and methylenedi(phenylamine) isomers (II-1) and in which the proportion of the secondary components (II-2) is at least 55% by weight.

The isolation (iv-2) of the low boiler mixture in step (iv) is preferably carried out simultaneously with the isolation (iv-1) of the mixture (II) in a column having a dividing wall or side stream offtake.

Furthermore, preference is given, in step (iv), to the isolation (iv-2) of the low boiler mixture from the overhead stream being carried out in a first distillation column, the resulting bottom stream being fed to a further (second) distillation column connected in series and (iv-1) the mixture (II) being separated off from the overhead stream from the further distillation column.

The simultaneous isolation of the low boiler mixture and of the mixture (II) by means of at least one dividing wall column or side stream column, in particular a dividing wall column, is particularly preferred according to the invention. Here, the low boiler mixture is separated off from the overhead stream and the mixture (II) is separated off from the side stream of the dividing wall column or side stream column.

The low boiler mixture is not recirculated into the recycle stream and is either discharged from the process of the invention or mixed with the MDA product mixture obtained in step (iv). The latter leads to a maximization of the yield.

The low boiler mixture is preferably discharged from the process. This has the advantage that target products having improved quality, i.e. in particular a low N-methyl-4,4'-methylenedianiline content, are obtained.

In a first preferred embodiment, the distillation to separate off (iv-2) the low boilers is carried out in a (first) conventional distillation column having from 2 to 15, preferably from 6 to 10, theoretical plates. The isolation (iv-1) of the mixture (II) is carried out in a further (second) distillation column having from 10 to 20, preferably from 13 to 16, theoretical plates. The distillation in the first distillation column is usually carried out at a pressure at the top of from 1 to 10 mbar, preferably from 1 to 3 mbar, and at a temperature of from 120 to 210° C., preferably from 135 to 177° C., particularly preferably from 147 to 166° C. The resulting bottom stream is then, in order to separate off (iv-1) the mixture (II), transferred into the further (second) distillation column as described above and a distillation is carried out at a pressure at the top of from 1 to 10 mbar, preferably from 4 to 6 mbar, and at a temperature of from 170 to 230° C., preferably from 200 to 215° C.

The distillation in step (iv) is preferably carried out using a dividing wall column or side stream column which has from 2 to 15, preferably from 6 to 10, theoretical plates in the upper region between the side stream and overhead stream and from 10 to 20, preferably from 13 to 16, theoretical plates in the lower region between the bottom and the side stream.

In a second preferred embodiment, a dividing wall column or side stream column as described above is used. In this embodiment, the distillation in step (iv) is carried out at a pressure at the top of from 1 to 10 mbar, preferably from 1 to 3 mbar, and a temperature of from 120 to 210° C., preferably from 135 to 177° C., particularly preferably from 147 to 166° C. in order to separate off (iv-2) the low boilers and at a side stream pressure of from 1 to 10 mbar, preferably from 4 to 6 mbar, and at a temperature of from 170 to 230° C., preferably from 200 to 215° C., in order to separate off (iv-1) the mixture (II). Here, the low boilers are separated off as overhead stream and the mixture (II) is separated off as side stream.

Particular preference is given to columns having internals such as Sulzer BXplus packings.

The mixture (II) which has been separated off is then, in step (v), recirculated to one of the zones (a) to (d), preferably zone (a).

This also encompasses the situation where the mixture (II) which has been separated off is not recirculated directly but can be temporarily stored in apparatuses suitable for this purpose. Furthermore, it is also possible, for example, for the mixture (II) which has been separated off in the process of the invention to be fed to a zone (a) to (d), preferably a zone (a), of a further plant or for a mixture (II) which has been separated off in a further plant to be fed to one of the zones (a) to (d), preferably (a), of the plant used according to the invention.

The polyamine mixture obtainable by the process of the invention, which comprises essentially 4,4'-methylenedi(phenylamine) and higher homologues of methylenedi(phenylamine), can usually be separated off as bottom stream from the column in step (iv).

The polyamine mixture obtained can then be passed to a phosgenation.

The polyamine mixture obtained by the process of the invention can also be combined again with the low boiler mixture which has been separated off and the two can be fed jointly to an optional phosgenation.

Preference is given to discharging the low boiler mixture from the process and feeding only the polyamine mixture obtained by the process of the invention to the optional phosgenation.

At least one acid catalyst is used in the process of the invention. Preference is given to using one acid catalyst. If this is a homogeneous catalyst, it is preferably added in admixture with aniline. Suitable homogeneous catalysts are mineral acids, in particular hydrochloric acid, sulfuric acid and phosphoric acid, particularly preferably hydrochloric acid. If hydrogen chloride is used as homogeneous catalyst, this can be used in gaseous form or as an aqueous solution.

If the acid catalyst is a heterogeneous catalyst, this is usually introduced into the reaction apparatuses of zones (b) to (d) of stage (i).

Advantageous heterogeneous catalysts are ion exchangers, clays, zeolites, silica-alumina or tungsten or molybdenum oxides on various supports such as $TiO_2$, $ZrO_2$, $HfO_2$, $SnO_2$ and $Al_2O_3$, with acidic ion exchangers being particularly advantageous. The catalysts mentioned can optionally be used in any combination.

As an alternative, it is also possible to introduce aniline in the form of an acidic salt into the process of the invention. In this case, the amine is preferably present in the form of a hydrochloride, sulfate or phosphate.

If a homogeneous catalyst is used, the molar ratio of aniline:catalyst is usually from 1:0.6 to 1:0.001, preferably from 1:0.3 to 1:0.05. In the case of heterogeneous catalysis, the catalyst is preferably present in an amount of from 1 to 99% by weight, preferably from 20 to 60% by weight, based on aniline. It is also possible to use a mixture of a homogeneous catalyst and a heterogeneous catalyst.

The process of the invention can also be carried out in the presence of a solvent. Particularly suitable solvents are ethers, optionally halogen-substituted aromatic and aliphatic solvents, water and mixtures thereof. Examples are benzene, toluene, monochlorobenzene, dichlorobenzene, dimethylformamide (DMF), tetrahydrofuran (THF) and diethyl isophthalate (DEIP). Particular preference is given to using monochlorobenzene. Preference is given to using aniline itself as solvent.

Formaldehyde can be fed to the process of the invention in the form of monomeric formaldehyde and/or in the form of higher homologues, known as poly(oxymethylene) glycols.

The molar ratio of aniline:formaldehyde is generally 1.75-10:1, preferably 2-4:1.

The process of the invention is preferably carried out continuously.

FIG. 1 illustrates a preferred embodiment of the process of the invention.

In the FIGURE, the reference numerals have the following meanings:
1 Mixing zone (a)
2 Condensation zone (b)
3 Rearrangement zone (c)
4 After-reaction zone (d)
5 Work-up zone (e)
6 Distillation column(s)
7 Introduction of aniline in admixture with catalyst
8 Introduction of formaldehyde
9 Discharge of 4,4'-MDA and higher homologues of MDA
10 Recirculation of the mixture (II) composed of 2,2'-MDA, 2,4'-MDA and 4,4'-MDA
11 Isolation of low boilers
12 Discharge of water and salts
13 Recirculation of aniline According to FIG. 1, the mixture (II) comprising 2,2'-MDA, 2,4'-MDA and 4,4'-MDA which has been separated off is recirculated 10 and mixed with aniline 7, to which an acid catalyst has been added, and formaldehyde 8 in a mixing zone (a) 1. A mixing chamber of a reaction mixing pump or a nozzle, which are located upstream of the condensation zone (b) 2, are preferably used here so that complete mixing occurs very rapidly. Rapid mixing decreases undesired parallel reactions.

A tube reactor or stirred reactor here represents, for example, a reaction zone which comprises a condensation zone (b) 2, a rearrangement zone (c) 3 and an after-reaction zone (d) 4. Aniline 7 or aniline hydrochloride is usually initially charged and a formalin solution 8 is fed in. The introduction can be effected directly into the reaction vessel or via a suitable mixing unit. In general, a suitable temperature profile is subsequently applied. After the condensation and rearrangement reactions, the reactor is emptied and the crude product is subsequently worked up. In a work-up zone (e) 5, the neutralization of the crude product and the discharge of water and salts 12 and also the isolation of aniline are carried out. The aniline which has been separated off is recirculated 13 to the mixing zone (a) 1. The crude product is then fed to a distillation in a distillation column 6. Here, the low boilers 11 are separated off. The mixture (II) composed of 2,2'-MDA, 2,4'-MDA and 4,4'-MDA which has been separated off is recirculated 10 to the mixing zone (a) 1 and the product composed of 4,4'-MDA and higher homologues of MDA is discharged 9.

The present invention is illustrated by the following examples.

EXAMPLES

Example 1 which is not according to the invention:
Recirculation of a 2,2'-/2,4'- and 4,4'-MDA isomer mixture, obtained by isolation by means of a distillation column having 40 theoretical plates, into the mixing zone (a) of an MDA plant as per FIG. 1 without prior isolation of a low boiler stream comprising secondary components formed 625 g of aniline (purity >99%) and 19 g of a recycle stream as per tab. 2 were placed in a stirred vessel and 131 g of a 32% strength hydrochloric acid were added thereto. 213 g/h of a 35.5% strength formalin solution were continuously mixed in at 60° C. over a period of 1 hour by means of a mixing pump. The mixing pump is located in the pumped circuit of the mixing vessel. The pump circulation was 25 l/h. After one hour, the introduction of formalin was stopped and the reaction mixture was heated to 90° C. and circulated by pumping for another 1.5 hours. The pump circulation was subsequently stopped and the reaction mixture was heated to 120° C. and dispersed further for 2 hours.

The fully reacted reaction mixture was cooled to 80° C. and then neutralized with aqueous sodium hydroxide solution (25% by weight). After the aqueous phase has been separated off, the organic phase is washed with water and the aniline is subsequently distilled off on a rotary evaporator at 1 mbar and an oil bath temperature of 100° C.

Table 1 shows the product composition after the work-up zone (e):

TABLE 1

| | |
|---|---|
| 2,2-MDA % by weight | 0.6 |
| 2,4-MDA % by weight | 9.4 |
| 4,4-MDA % by weight | 59.1 |
| 3-ring MDA % by weight | 20.3 |
| 4-ring MDA % by weight | 5.6 |
| N-Methyl-MDA % by weight | 0.120 |

The proportion of secondary components having a boiling point equal to or greater than that of aniline and less than that of 2,2''-MDA in the product mixture as per tab. 1 was about 500 ppm.

To separate off the 2,2'-/2,4'- and 4,4'-MDA recycle stream, the product mixture as per tab. 1 was fed at plate 20 into a distillation column having 40 theoretical plates. At a pressure at the top of 10 mbar and a temperature at the top of 224° C., a recycle stream having the following composition was obtained at the top of the column at a reflux ratio of 9 g/g:

TABLE 2

| | |
|---|---|
| 2,4'-MDA | 73.5% |
| 2,2'-MDA | 11.5% |
| 4,4'-MDA | 13.9% |
| Sum of secondary components | 1.1% |

The composition of this recycle stream corresponds to the composition of the recycle stream which was introduced into the mixing zone (a) at the beginning of the experiment.

The product mixture obtained at the bottom of the column has the following product composition:

TABLE 3

| | |
|---|---|
| 2,2-MDA % by weight | 0.07 |
| 2,4-MDA % by weight | 6.5 |
| 4,4-MDA % by weight | 61.2 |
| 3-ring MDA % by weight | 21.3 |
| pMDA % by weight | 10.8 |
| N-Methyl-MDA % by weight | 0.125 |

Example 1 according to the invention:
Recirculation of a 2,2'-/2,4'- and 4,4'-MDA isomer mixture, obtained by isolation by means of a first distillation column and a second distillation column having 8 and 15, respectively, theoretical plates, into the mixing zone (a) of an MDA plant as per FIG. 1 with prior isolation of a low boiler stream comprising secondary components formed and discharge of the low boiler stream from the process 720 g of aniline (purity>99%) and 19 g of a recycle stream as per tab. 5 were placed in a stirred vessel and 154 g of a 32% strength hydrochloric acid were added thereto. 253 g/h of a 35.5% strength formalin solution were continuously mixed in at 60° C. over 1 hour by means of a mixing pump. The mixing pump is located in the pumped circuit of the mixing vessel. The pumped circulation was 25 l/h. After 1 hour, the introduction of formalin was stopped and the reaction mixture was heated to 90° C. and circulated by pumping for another 1.5 hours. The pumped circulation was subsequently stopped and the reaction mixture was heated to 120° C. and dispersed further for 2 hours.

The fully reacted reaction mixture was cooled to 80° C. and then neutralized with aqueous sodium hydroxide solution (25% by weight). After the aqueous phase has been separated off, the organic phase is washed with water and the aniline is subsequently distilled off in a rotary evaporator at 1 mbar and an oil bath temperature of 100° C.

Table 4 shows the product composition after the work-up zone (e):

TABLE 4

| 2,2-MDA % by weight | 0.4 |
|---|---|
| 2,4-MDA % by weight | 8.8 |
| 4,4-MDA % by weight | 59.5 |
| 3-ring MDA % by weight | 21.4 |
| 4-ring MDA % by weight | 6.6 |
| N-Methyl-MDA % by weight | 0.096 |

The proportion of secondary components having a boiling point equal to or greater than that of aniline and less than that of 2,2'-MDA in the product mixture as per tab. 4 was about 500 ppm.

To separate off the 2,2'-/2,4'- and 4,4'-MDA recycle stream, the product mixture as per tab. 4 was fed at plate 5 into a first distillation column having 8 theoretical plates. At a pressure at the top of 2 mbar and a temperature at the top of 152° C., a low boiler stream having a content of secondary components of 86% was obtained at a reflux ratio of 150 g/g and discharged from the process.

The product stream obtained at the bottom of the first column is fed at plate 10 into a second distillation column having 15 theoretical plates. At a pressure at the top of 5 mbar and a temperature at the top of 207° C., a recycle stream having the following composition is obtained at the top of the column at a reflux ratio of 26 g/g:

TABLE 5

| 2,4'-MDA | 75.5% |
|---|---|
| 2,2'-MDA | 11.8% |
| 4,4'-MDA | 12.6% |
| Sum of secondary components | 0.1% |

The composition of this recycle stream corresponds to the composition of the recycle stream which was introduced into the mixing zone (a) at the beginning of the experiment.

The product mixture obtained at the bottom of the second column has the following product composition:

TABLE 6

| 2,2-MDA % by weight | <0.01 |
|---|---|
| 2,4-MDA % by weight | 6.3 |
| 4,4-MDA % by weight | 61.2 |
| 3-Kern-MDA % by weight | 22.2 |
| p-MDA % by weight | 10.2 |
| N-Methyl-MDA % by weight | 0.100 |

The content of N-methyl-MDA could be reduced from 0.125% to 0.100%. This corresponds to a decrease in the undesirable secondary components of 20%.

Example 2 according to the invention:

Recirculation of a 2,2'-/2,4'- and 4,4'-MDA isomer mixture, obtained by isolation by means of a first distillation column and a second distillation column having 10 and 15, respectively, theoretical plates, into the mixing zone (a) of an MDA plant as per FIG. 1 with prior isolation of a low boiler stream comprising secondary components formed and recirculation of the low boiler stream into the product stream from the second distillation column 690 g of aniline (purity>99%) and 19 g of a recycle stream as per tab. 8 were placed in a stirred vessel and 144 g of a 32% strength hydrochloric acid were added thereto. 235 g/h of a 35.5% strength formalin solution were continuously mixed in at 60° C. over a period of 1 hour by means of a mixing pump. The mixing pump is located in the pump circuit of the mixing vessel. The pumped circulation was 25 l/h. After 1 hour, introduction of the formalin solution was stopped and the reaction mixture was heated to 90° C. and circulated by pumping for another 1.5 hours. The pumped circulation was subsequently stopped and the reaction mixture was heated to 120° C. and dispersed further for 2 hours.

The fully reacted reaction mixture was cooled to 80° C. and then neutralized with aqueous sodium hydroxide solution (25% by weight). After the aqueous phase has been separated off, the organic phase is washed with water and the aniline is subsequently distilled off on a rotary evaporator at 1 mbar and an oil bath temperature of 100° C.

Table 7 shows the product composition after the work-up zone (e):

TABLE 7

| 2,2-MDA % by weight | 0.5 |
|---|---|
| 2,4-MDA % by weight | 9.0 |
| 4,4-MDA % by weight | 58.8 |
| 3-ring MDA % by weight | 21.2 |
| 4-ring MDA % by weight | 6.5 |
| N-Methyl-MDA % by weight | 0.086 |

The proportion of secondary components having a boiling point equal to or greater than that of aniline and less than that of 2,2"-MDA in the product mixture as per tab. 7 was about 500 ppm.

To separate off the recycle stream, the product mixture as per tab. 7 was fed at plate 4 into a first distillation column having 10 theoretical plates. At a pressure at the top of 2 mbar and a temperature at the top of 150° C., a low boiler stream having a content of secondary components of 82% was obtained at a reflux ratio of 500 g/g.

The product stream obtained at the bottom of the first column is fed at plate 10 into a second distillation column having 15 theoretical plates. At a pressure at the top of 4 mbar and a temperature at the top of 202° C., a recycle stream having the following composition is obtained at the top of the column at a reflux ratio of 22 g/g:

TABLE 8

| 2,4'-MDA | 75.0% |
|---|---|
| 2,2'-MDA | 12.4% |
| 4,4'-MDA | 12.6% |
| Sum of secondary components | <0.01% |

The composition of this recycle stream corresponds to the composition of the recycle stream which was introduced into the mixing zone (a) at the beginning of the experiment.

The product mixture obtained at the bottom of the second column was mixed with the overhead stream from the first column (low boiler stream). The resulting final product mixture has the following product composition:

TABLE 9

| | |
|---|---|
| 2,2-MDA % by weight | 0.02 |
| 2,4-MDA % by weight | 6.3 |
| 4,4-MDA % by weight | 60.6 |
| 3-ring MDA % by weight | 22.0 |
| p-MDA % by weight | 10.9 |
| N-Methyl-MDA % by weight | 0.09 |

The content of N-methyl-MDA could be reduced from 0.125% to 0.09%. This corresponds to a decrease in the undesirable secondary components of 28%.

The invention claimed is:

1. A process for preparing an aromatic polyamine mixture comprising 4,4'-methylenedi(phenylamine) and higher homologues of methylenedi(phenylamine), the process comprising
    (i) reacting aniline with formaldehyde in the presence of an acid catalyst to form a crude product mixture (I) in a plant which comprises a mixing zone (a), a condensation zone (b), a rearrangement zone (c) and optionally an after-reaction zone (d);
    (ii) neutralizing the crude product mixture (I) obtained in (i) and removing salts thus formed, to obtain a crude product mixture (II);
    (iii) separating aniline from the crude product mixture (II) obtained in (ii), to obtain separated aniline and a crude product mixture (III), and optionally recirculating the separated aniline to the mixing zone (a); then
    (iv) distilling the crude product mixture (III) obtained in (iii) wherein the distilling comprises
        (iv-1) isolating a mixture (II) consisting of methylenedi(phenylamine) isomers (II-1) and secondary components (II-2) which are different therefrom, where, based on (II-1), a proportion of 4,4'-methylenedi(phenylamine) is from 8 to 20% by weight and, based on (II), a proportion of secondary components (II-2) is not more than 0.3% by weight, and
        (iv-2) isolating a low boiler mixture which consists of secondary components (II-2) and methylenedi(phenylamine) isomers (II-1) and in which a proportion of the secondary components (II-2) is at least 55% by weight; and
    (v) recirculating the mixture (II) to one of the zones (a) to (d),
    wherein the aromatic polyamine mixture has a content of 4,4'-methylenedi(phenylamine) and higher homologues of methylenedi(phenylamine) of greater than 85% by weight.

2. The process according to claim 1, wherein, in the distilling (iv), the isolating (iv-2) is carried out simultaneously with the isolating (iv-1) in a column having a dividing wall or a side stream offtake.

3. The process according to claim 1, wherein, in the distilling (iv),
    the isolating (iv 2) is effected from an overhead stream from a first distillation column,
    a bottom stream obtained is fed to a further successive distillation column and
    the mixture (II) is separated off from the overhead stream from the further distillation column.

4. The process according to claim 1, wherein a dividing wall or side stream column which has from 2 to 15 theoretical plates in an upper region between a side stream and an overhead stream and from 10 to 20 theoretical plates in a lower region between a bottom stream and the side stream is used for the distilling (iv).

5. The process according to claim 1, wherein the distilling (iv) is carried out in
    a first distillation column having from 2 to 15 theoretical plates for the isolating (iv-2) and
    a further distillation column having from 10 to 20 theoretical plates for the isolating (iv-1).

6. The process according to claim 1, wherein the distilling (iv) is carried out at
    a pressure at a top of a distillation column of from 1 to 10 mbar and a temperature of from 120 to 210° C. for separating off the low boiler mixture and
    a side stream pressure of from 1 to 10 mbar and a temperature of from 170 to 230° C. for separating off the mixture (II).

7. The process according to claim 5, wherein, in the first distillation column, the distilling (iv) is carried out at a pressure at a top of the first distillation column of from 1 to 10 mbar and at a temperature of from 120 to 210° C., and
    in the further distillation column, the distilling (iv) is carried out at a pressure at a top of the further distillation column of from 1 to 10 mbar and at a temperature of from 170 to 230° C.

8. The process according to claim 1, wherein the low boiler mixture is discharged from the process.

9. The process according to claim 1, wherein the mixture (II) is recirculated to the mixing zone (a).

10. The process according to claim 1, wherein the aromatic polyamine mixture is separated as a bottom stream from a column in the distilling (iv).

* * * * *